United States Patent [19]

Boscher et al.

[11] Patent Number: 4,807,466

[45] Date of Patent: Feb. 28, 1989

[54] METHOD AND APPARATUS FOR DETERMINING THE CHARGING OF CHARCOAL FILTERS

[75] Inventors: Jörg Boscher, Preetz; Karl-Ernst Biehl, Hanau, both of Fed. Rep. of Germany

[73] Assignee: Honeywell-Elac-Nautik GmbH, Kiel, Fed. Rep. of Germany

[21] Appl. No.: 240

[22] Filed: Jan. 2, 1987

[30] Foreign Application Priority Data

Jan. 18, 1986 [EP] European Pat. Off. .......... 86100623

[51] Int. Cl.$^4$ ............................................. G01N 29/00
[52] U.S. Cl. .......................................... 73/38; 73/599
[58] Field of Search ................... 73/38, 29, 599, 571; 340/607

[56] References Cited

U.S. PATENT DOCUMENTS

| | | | |
|---|---|---|---|
| 4,111,034 | 9/1978 | Hübner | 73/23 |
| 4,237,726 | 12/1980 | Peterson et al. | 73/73 |
| 4,472,356 | 9/1984 | Kolesar | 422/88 |
| 4,481,820 | 11/1984 | Thomann | 73/599 X |
| 4,530,706 | 7/1985 | Jones | 55/275 |

FOREIGN PATENT DOCUMENTS

| | | | |
|---|---|---|---|
| 2525567 | 12/1976 | Fed. Rep. of Germany | |
| 48588 | 4/1938 | France | |
| 879425 | 11/1981 | U.S.S.R. | 73/29 |

OTHER PUBLICATIONS

Longstaff, B. G. et al., *Measurement of Acoustic Absorption by Means of Twin Impedance Tubes*, in Noise, Shock & Vibration Conference, Melbourne, Aust., May 1974, pp. 154–160.

*Primary Examiner*—Stewart J. Levy
*Assistant Examiner*—Joseph W. Roskos
*Attorney, Agent, or Firm*—Clyde C. Blinn

[57] ABSTRACT

For determining the charging of a charcoal filter with gases and vapors the acoustical and the electrical impedance of the charcoal layer are measured. The more the filter is charged the greater will be the density of the charcoal layer and therewith its acoustical conductivity. The charging of a charcoal layer with water vapor results in an increase of the acoustical as well as of the electrical conductivity. By comparing the acoustical impedance and the electrical impedance respectively of a partially charged charcoal layer with the impedance of a non-charged charcoal layer and by subsequent comparison of the impedance changes caused by such charging the influence of water vapor can be eliminated. A signal is generated corresponding to the charging of the charcoal filter with other vapors and gases which signal may be used for indicating the condition of the filter and for generating an alarm if the filter becomes exhausted.

10 Claims, 2 Drawing Sheets

METHOD AND APPARATUS FOR DETERMINING THE CHARGING OF CHARCOAL FILTERS

BACKGROUND AND SUMMARY OF THE INVENTION

The invention relates to a method for determining the charging of a charcoal filter with gases or vapors and also relates to an apparatus for applying this method. Charcoal filters are used for removing gases and vapor from air. Therewith the ability of charcoal and in particular of impregnated charcoal is used to bind gases and vapors by physical and chemical absorption. When the filer is charged or loaded with gases and vapors the filtering capacity of the filter is reduced until the filter becomes inactive when saturation charge is reached. If this status is reached gases and vapors are able to move through the filter. In particular when filtering air containing toxic gases or vapors it is necessary to indicate in time before reaching the saturation that the filter is being exhausted.

Two groups of methods are known for determining the charging condition of a charcoal filter. The first group requires disassembly of or manipulation at the filter inlet and outlet. This group includes the weighting of the filter and the so called $CO_2$ pulse test (see NRL report 6793 "The $CO_2$ Pulse Technique for Determining Residual Gas Life of Charcoals Beds"). These methods cannot be performed when the filter is in use and don't provide a real time determination of the actual saturation condition of the filter.

A second group of methods permits the determination of the saturation level under conditions like in actual use or during simulation. In accordance with these methods gas detectors or gas indicators are provided in the filter. They provide an indication when a predetermined gas because of a reduced filtering capability of the filter can move to the location of the detector A disadvantage of these methods that these detectors or indicators respond only to particular gases or vapors. If instead of these vapors another gas or vapor is present in the air flow, an exhaust of the filter will not be recognized. Because of the combined adsorptive and chemical adsorptive effect impregnated charcoal filters provide protection against all gas like or vapor like toxic materials in air. The detectors and indicators mentioned before, however, only have a limited detection band width.

It has been proposed to embed into the charcoal filter, detectors made of $SnO_2$ or $ZrO_2$. These detectors permit the indication of burnable gases and accordingly can indicate the flow of carbon monoxide or methane. They are not suitable, however, to determine in ABC protective filters the passing through of nerve toxin, blood toxin or pulmonary toxin. The same limitation is valid for color indicators which are provided within the filter behind a window. With these indicators the chemical reaction of a reactive with the gas or vapor which has to be determined is indicated by means of a change of color. This change of color must be determined by looking onto the indicator. An automation of the method is possible in principle however requires a relatively complicated apparatus.

It is the object of the invention to automatically indicate the saturation level or the increase above a predetermined saturation level within a charcoal filter. The indication should be continuously present during the normal operation of the filter or during operation pauses. The method should determine and indicate the charging condition independently from the type of the adsorptively or chemisorptively bound gases or vapors. In addition sometimes it is desired to separate in the indication the water vapor content of the filter charge from the charge portion of other gases or vapors.

DESCRIPTION OF THE INVENTION

Figure 1:
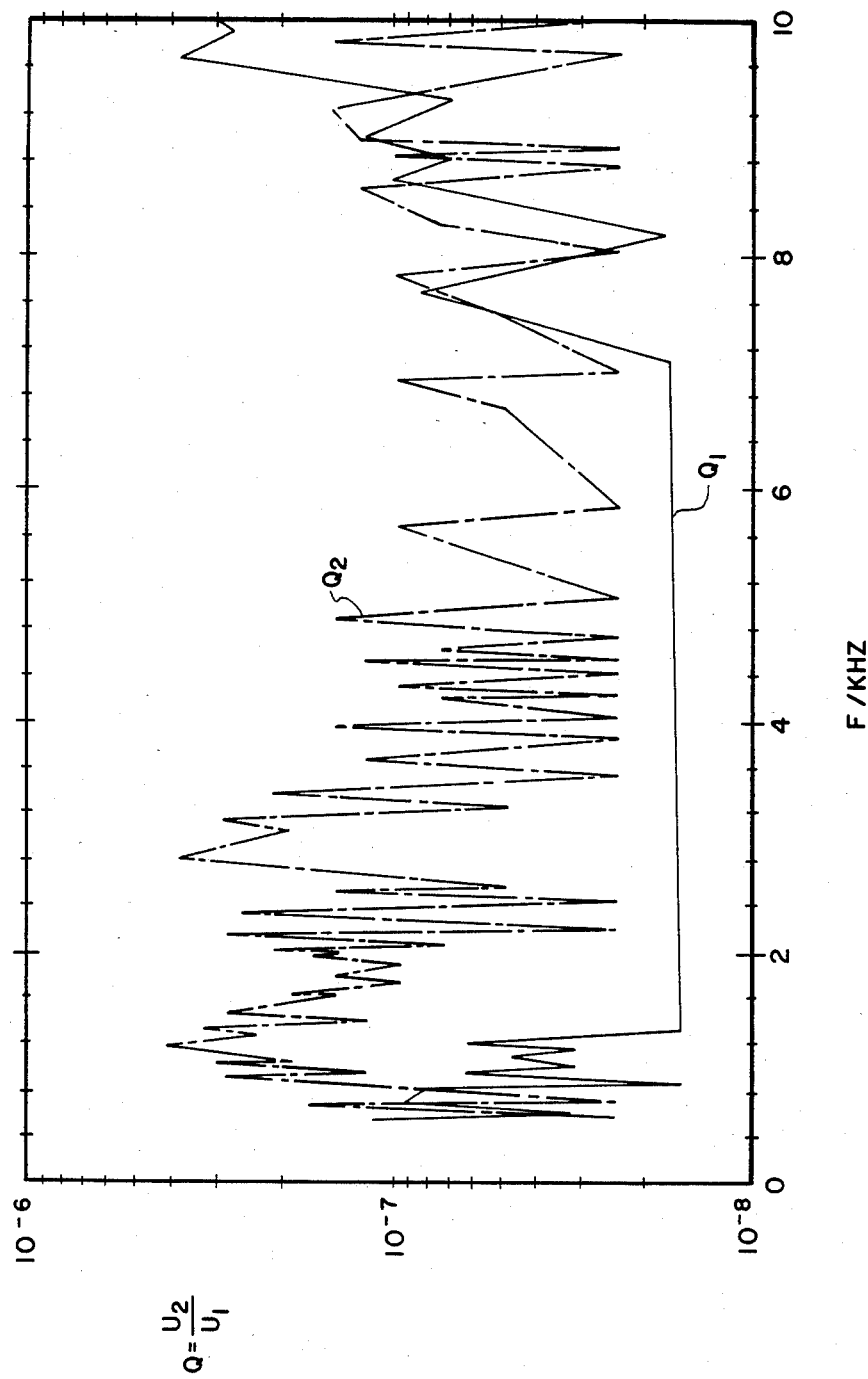
FIG. 1 shows a graphical representation of certain functions.

The acoustical and the electrical impedance are physical values which change with the charging of an impregnated charcoal filter. By adsorption and chemical absorption of gases and vapors in the microporous volume of the charcoal body the mass of the medium is increased without a simultaneous increase of the macro volume. This means an increase of the average density of the medium. This increase of the density in turn leads to a change of the acoustical transmission properties of the medium. FIG. 1 shows the acoustical transmission Q of a charcoal layer dependent on the sound frequency F for two different charging conditions with a test substance DMMP. The acoustical conductivity Q is given by the amplitude relation of the acoustical receiver signal $U_2$ to the acoustical transmitter signal $U_1$. Curve $Q_1$ is the curve with an uncharged charcoal and curve $Q_2$ shows the situation of the charcoal is saturated. These measuring curves show that the transmissivity of the charcoal charged with 10% of weight DMMP and therewith being almost saturated is essentially increased compared to the uncharged condition in the frequency range of 1 to 7 kHz. There was no change of the electrical impedance caused by the charging with DMMP.

A charging of the charcoal with water vapor in principle has the same effect on the acoustical properties as a charging with DMMP. In addition, however, there is a change of the electrical impedance. This change is generated by solution processes during the interaction of the water vapor with the metal salt impregnation of the charcoal.

A charging with water vapor therefore is characterized by a simultaneous change of the acoustical and the electrical impedance. If the air is charged by gases or vapors other than water vapor there is effected only a change of the acoustic impedance. Since this change is caused by an increase of the mass or the density respectively any effects caused by different gases or vapors bound by adsorption either simultaneously or subsequently are superimposed and added.

By calibration measurements with uncharged charcoal the dependency of the electrical and the acoustical impedance can be determined. Measuring each of these two impedances permits determination of the charge with water vapor. If the filter in addition to water vapor is also charged with other gases and vapors the measuring of the electrical impedance furthermore permits a determination of the portion of water vapor. Therewith by means of a calibration measurement the portion of water vapor influencing the acoustical impedance can be determined. By forming a differential of suitable properties such as mass or density derived from the acoustical impedance the charging portion caused by gases and vapors which is independent from water vapor can be separated.

In a preferred embodiment of the method it is possible to achieve the objective without such kind of calibration measurements. By using a volume of uncharged charcoal for comparison purposes provided in a hermetically sealed chamber reference values or calibration values may be generated simultaneously with the actual measuring values and these reference values can be processed electrically in the same manner as the actual measuring values. Preferred improvements of the method and an embodiment of an apparatus for carrying out the method are described in the subclaims.

Figure 2:
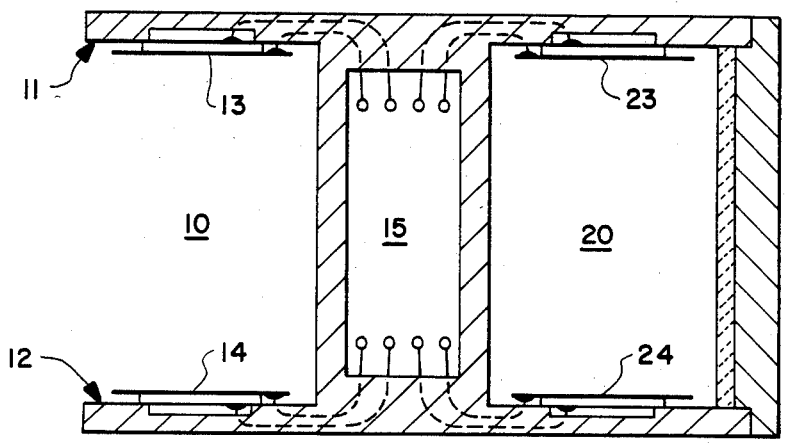
FIG. 2 shows schematically an appratus for applying the method according to the invention.

The main components of the apparatus shown in FIG. 2 are a measuring chamber 10 and a reference chamber 20. Measuring chamber 10 is open at two opposite sides and at its front surface. The entire apparatus is placed within the charcoal filter in such a way that the measuring chamber is filled with charcoal. The apparatus is located such that the flow direction of air within the filter is parallel to the two chamber walls 11, 12 and is perpendicular with respect to the plane of the drawing. The charcoal volume within measuring chamber 10 is chosen such that the measurement of the degree of charging of this partial volume is proportional to the degree of saturation or the residual live time of the entire filter.

Reference chamber 20, however, contains uncharged charcoal from the same charge as the filter which in fresh condition is filled into the chamber and is hermetically sealed therein. The packing density of the charcoal in both chambers is identical. Both chambers have an electroacoustic transducer 13 and 23 respectively as a transmitter and comprise a second transducer 14 and 24 respectively used as receiver. The transducers consist of piezoceramic discs 136, 146 and 236, 246 respectively onto which a metal diaphragm 137, 147; 237, 247 is bonded. The metal diaphragm simultaneously is used as electrode for measuring the electrical impedance of the charcoal layer located between the transducers.

In a third chamber 15 electronic components for power supply, signal generation and signal processing are located. The electroacoustic transducers 13 and 23 are controlled such that they transmit an acoustical signal of predetermined sound strength, e.g., in the frequency range between 1 and 7 kHz. The transducers 14 and 24 located on the opposite side receive an acoustic signal with a sound strength which is reduced dependent on the acoustical impedance of the charcoal layer. The relation of the electrical signal generated in the receiver to the control signal of the transmitter transducer is a measure for the acoustical impedance of the measuring volume.

Figure 3:
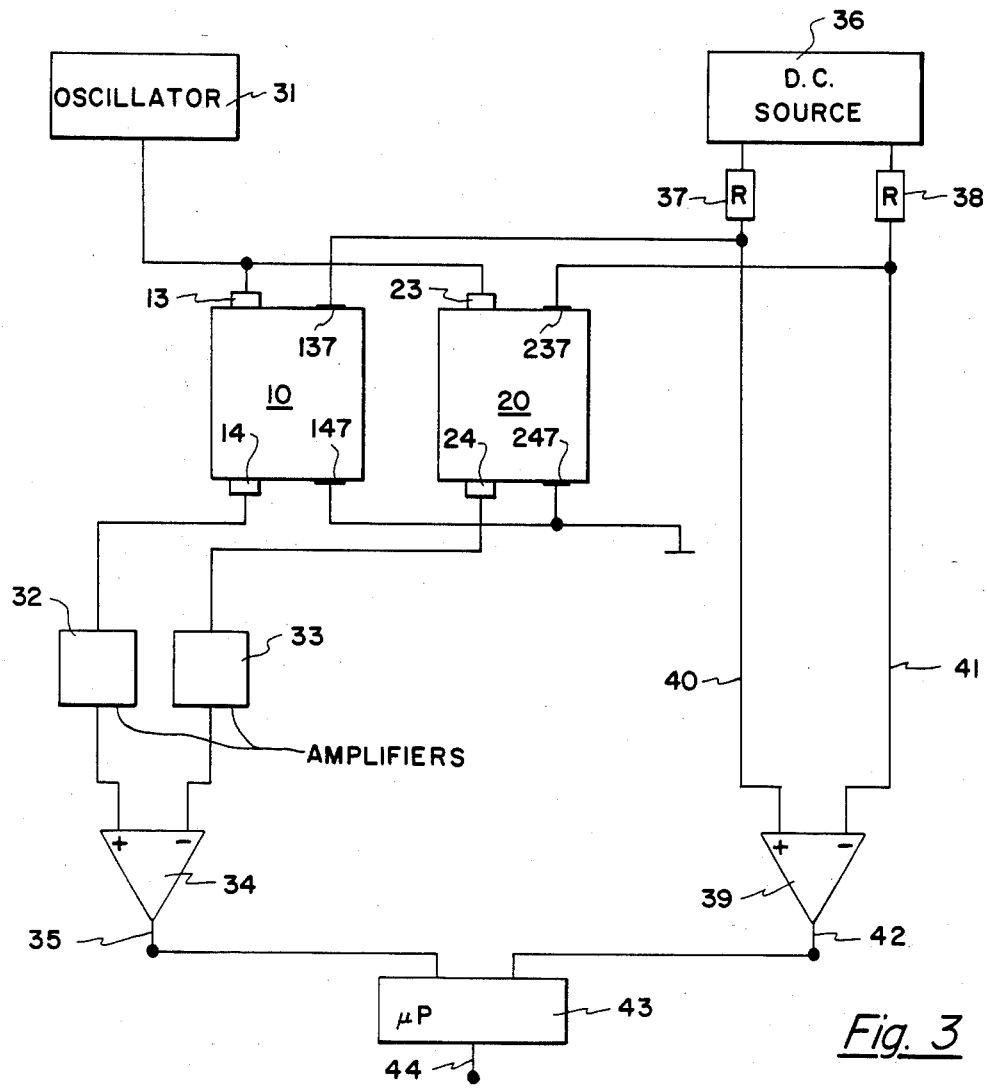
FIG. 3 shows a block diagram of an associated control and evaluation circuit.

In FIG. 3 the measuring chamber 10 and the reference chamber 20 are shown together with the associated control and evaluation circuits. Electrodes 137, 147; 237, 247 used for measuring the electrical impedance are shown separately from transducers 13, 14, 23 and 24 for better understanding of the drawing. These electrodes, however, can be part of the transducers as shown in FIG. 2. Transmitter transducer 13 in measuring chamber 10 and transmitter transducer 23 in reference chamber 20 are commonly supplied by oscillator 31 with an electrical signal in the frequency range between 1 and 7 kHz. For this purpose a single frequency in this frequency range may be generated or the signal is modulated across the entire frequency range. The acoustoelectrical receiver transducers 14 and 24 receive acoustical signals which are attenuated dependent on the acoustical impedance of the charcoal layer in the two chambers. The receiving transducers transduce the received acoustical signals into electrical signals and feed these electrical signals to the two inputs of a subtracting circuit 34 via amplifiers 32 and 33 respectively. At the output 35 of subtracting or difference forming circuit 34 a signal is available which corresponds to the difference of the acoustic impedance in the two chambers and therewith is characteristic for the change of the acoustic impedance in the measuring chamber 10 caused by the charging of the filter with water vapor or other vapors and gases in relation to the acoustical impedance of a non-charged filter according to the condition in the reference chamber 20.

A DC source 36 feeds via resistor 37 and 38 a voltage to electrode pairs 137, 147 and 237, 247. The current flowing through the filter layer located between the electrodes of each pair of electrodes and therewith the current through resistor 37 and 38 changes dependent on the electrical impedance of the filter layer within measuring chamber 10 and reference chamber 20 respectively. Therefore the voltage drop across resistors 37 and 38 and therewith the voltage fed to the two inputs of substracting circuit 39 via lines 40 and 41 is a measure for the electrical impedance of the charcoal layer within measuring chamber 10 and reference chamber 20 respectively. Subtracting circuit 39 delivers at its output 42 a signal which characterizes the change of the electrical impedance within measuring chamber 10 because of the charging of its charcoal layer with water vapor. The charging of the charcoal volume in measuring chamber 10 with other gases or vapors has as mentioned above no influence on the electrical impedance. The signal on line 35 dependent on the total charging of the measuring chamber and the signal on line 42 depending only on the water vapor charge of the measuring cell are fed to an evaluating circuit 43 including an analog to digital converter and a microprocessor. In this evaluation circuit 43 the two above mentioned signals are compared and an output signal is derived which depends only on the charging of the measuring chamber with the filtered gases or vapors. This signal is available at terminal 44. It characterizes the charging level of the filter and may be used for indicating or generating an alarm signal. The A/D conversion in another embodiment may already be provided after the generation and amplification of the signals generated by the receiving transducers 14, 24 or generated across resistor 37 and 38 respectively. This conversion into digital signals in this case is made before a difference is formed between the reference chamber signals and the measuring chamber signals. In this case subtracting circuits 34 and 39 together with evaluating circuit 43 and perhaps also together with oscillator 31 and a stabilized DC supply circuit might be realized by a single microprocessor.

By comparing the electrical impedances of the measuring chamber and the reference chamber on the one side and the acoustical impedances of the measuring chamber and the reference chamber on the other side the charging of the measuring chamber with foreign substances or impurities can be determined. The difference with respect to the electrical impedance is derived from the charge with water vapor and the difference with respect to the electrical impedance originates from the charge with all kinds of gases or vapors including water vapor. By comparing the acoustical and the electrical impedance changes a signal is derived which depends alone from the charging condition of the filter with gases or vapors other than water vapor. This signal therewith indicates the degree of exhaustion of the filter. By comparing the output signal at terminal 44 with a preset limit an acoustical or optical alarm might be released if this limit is exceeded and therewith an exhaustion of the filter is indicated. The user of the filter then becomes aware that the filter is exhausted and should be replaced.

In a further embodiment the measuring apparatus might be provided in a shunt located in parallel to the filter and might be rigidly integrated into the system. For instance, the tube walls of a shunt tube in one portion may simultaneously form the measuring chamber. In such an arrangement it has to be recognized that the degree of charging of the measuring volume in the shunt tube really is proportional to the degree of charging of the filter itself which is connected in parallel to the shunt. This can be accomplished by suitable guiding means for the air and an adapted thickness of the charcoal layer within the shunt tubing.

Instead of permanently measuring the acoustical and the electrical impedance of a non-charged filter as shown in the embodiment, these reference values might be determined only once and can be stored as a reference curve or a group of reference values which afterwards are compared with the actual measuring values of the electrical and the acoustical impedance of the charcoal layer within the measuring chamber. In this case the reference chamber 20 and the associated electrical circuitry is no longer required. However it has to be recognized that the reference values of the acoustical and the electrical impedance depend on the type and the packing density of the charcoal within the measuring chamber. If a different type of coal is used or the charcoal has a different grain size it is necessary to provide a correction of the associated reference values. The method can be performed in such a way that the measuring value of the electrical impedance is compared with a calibrating curve which shows the electrical impedance dependent on the water content of the filter. From this comparison the water content of the filter is determined. Subsequently, by means of a second calibration curve, the acoustical impedance is calculated. This second calibration curve shows the acoustical impedance dependent on the water content of the filter. The value of the acoustical impedance at the determined water content is subtracted from the measuring value of the acoustical impedance which does not only depend on the charging with water vapor but also upon the charging with other vapors and gases. From this comparison a differential value is obtained which depends on the charging with such other gases and vapors. The use of such calibration curves and the consideration of the type and grain size of the charcoal can be eliminated if as shown in the embodiment a measuring chamber and a reference chamber are simultaneously filled with the same charcoal and the impedance measurement is continuously performed at both chambers and the measuring values are compared.

The determination of the electrical impedance or impedance change respectively cannot only be accomplished by measuring the ohmic resistance but other impedance measuring circuits might be used, for instance such for measuring the reactance or reactance components. The use of AC voltages and AC current might be useful in order to avoid electrochemical processes at the electrodes in particular to prevent depositions at the electrodes.

THE EMBODIMENTS OF THE INVENTION IN WHICH AN EXCLUSIVE PROPERTY OR RIGHT IS CLAIMED ARE DEFINED AS FOLLOWS:

1. A method for determining the charging of a charcoal filter with gases and vapors, comprising the following steps:
   a. measuring the acoustical impedance of a partial volume of the filter;
   b. comparing the measured acoustic impedance with a reference value corresponding to a non-charged filter;
   c. measuring the electrical impedance of this partial volume of the filter;
   d. comparing the measured electrical impedance with a reference value derived from a non-charged filter; and
   e. determining an electrical signal depending on the charging by comparing the change of the electrical impedance with the change of the acoustical impedance in relation to the associated reference values.

2. A method according to claim 1, in that the reference values of the electrical and the acoustical impedance are provided in the form of reference curves which show the dependency of the concerned impedance on the water content of the filter.

3. A method according to claim 1 or 2, comprising the additional steps:
   a. the measuring value of the electrical impedance is compared with a calibration curve which shows the electrical impedance dependent on the water content of the filter and from this comparison the water content of the filter is calculated;
   b. by means of a second calibration curve the acoustical impedance is calculated with said second calibration curve showing the acoustical impedance dependent on the water content; and
   c. the value of the electrical impedance is subtracted from the value of the acoustical impedance and a differential value is calculated which depends on the charging of the charcoal filter with other gases and vapors.

4. A method according to claim 1, wherein step e is a continuous determination of the reference values by measuring the acoustical and the electrical impedance of a non-charged reference volume of charcoal.

5. Apparatus for performing the method of claim 4 comprising:
   a. a measuring chamber filled with a layer of the charcoal to be investigated;
   b. a reference chamber filled with a layer of non-charged charcoal;
   c. in said measuring chamber a first electroacoustic transmitting transducer and a first acoustoelectrical receiving transducer together with two first electrodes;
   d. in the reference chamber a second electroacoustic transmitting transducer and a second acoustoelectrical receiving transducer together with two second electrodes; whereat
   e. in each chamber the charcoal layer separates the transmitting transducer from the receiving transducer and said electrodes;
   f. the first and second transmitting transducers are connected to a signal generator;
   g. the first receiving transducer is connected to a first input of a first comparator via a first amplifier and the second receiving transducer is connected to the second input of the first comparator via a second amplifier;

h. said first comparator comparing a first measuring signal corresponding to the acoustical impedance of the charcoal layer in the measuring chamber with a second measuring signal corresponding to the acoustical impedance of the charcoal layer in the reference chamber;

i. in the measuring chamber the two first electrodes are connected to a voltage source and to a first current measuring circuit generating a signal corresponding to the electrical impedance of the charcoal layer in the measuring chamber;

j. in the reference chamber the two second electrodes are connected to said voltage source and to a second current measuring circuit generating a signal corresponding to the electrical impedance of the charcoal layer in the reference chamber;

k. a second comparator receives the two electrical signals corresponding to the electrical impedance of the charcoal layer in the measuring chamber and in the reference chamber respectively; and l. an evaluation circuit receives at its one input the electrical signal from the output of the first comparator said signal corresponding to the difference of acoustical impedance of the two charcoal layers, and said evaluation circuit receives at a second input the output signal of the second comparator corresponding to the difference of the electrical impedance of the two charcoal layers, and said evaluating circuit providing at its output a signal which is corrected with respect to the charge of the filter with water vapor and which therewith depends only on the charge of the charcoal layer in the measuring chamber with other vapors and gases.

6. The apparatus of claim 5, wherein the measuring chamber at its front surface and at two opposite sides is open for being filled with charcoal and where the reference chamber is hermetically sealed and filled with non-charged charcoal and whereat a third chamber comprises the electronic components for power supply, signal generation, and signal processing.

7. Apparatus according to claim 5, whereat the measuring chamber is an integral portion of a shunt tube provided in parallel to the filter with a part of the air flow flowing through said shunt tube.

8. A method according to one of the claims 1, 2 or 4 wherein the acoustical impedance is measured in a frequency range which depends on the type and grain size of the charcoal and from this measuring value an average value is derived.

9. Apparatus for performing the method according to claim 1 whereat:

a. in a measuring chamber separated by a charcoal layer there are provided an electroacoustic transmitting transducer and an acoustoelectrical receiving transducer together with two further electrodes;

b. the transmitting transducer is connected to a signal generator and the receiving transducer is connected to a comparator via an amplifier, with said comparator comparing a measuring signal corresponding to the acoustical impedance of the charcoal layer in the measuring chamber, with a corresponding signal indicating the acoustical impedance in a non-charged charcoal layer;

c. the two electrodes are connected to a voltage source and to a current measuring circuit which generates a measuring signal depending on the electrical impedance of the charcoal layer in the measuring chamber;

d. a second comparator is supplied with this measuring signal corresponding to the electrical impedance of the charcoal layer in the measuring chamber and is furthermore supplied with a signal corresponding to the electrical impedance of a non-charged charcoal layer; and e. an evaluating circuit receives at its input the electrical signals corresponding to the change of the acoustical and the electrical impedance dependent on the charging condition of the filter and which evaluation circuit delivers at its output an output signal which is corrected with respect to the charge of the filter with water vapor and which depends only from the charge with other vapors and gases.

10. Apparatus according to claim 9 in that the measuring chamber is an integral portion of a shunt tube provided in parallel to the filter with a part of the air flow flowing through said shunt tube.

* * * * *